(12) United States Patent
Taimisto et al.

(10) Patent No.: US 7,959,630 B2
(45) Date of Patent: Jun. 14, 2011

(54) MEDICAL PROBES FOR CREATING AND DIAGNOSING CIRCUMFERENTIAL LESIONS WITHIN OR AROUND THE OSTIUM OF A VESSEL

(75) Inventors: Miriam H. Taimisto, San Jose, CA (US); Josef V. Koblish, Palo Alto, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 32 days.

(21) Appl. No.: 12/209,124

(22) Filed: Sep. 11, 2008

(65) Prior Publication Data
US 2009/0018534 A1 Jan. 15, 2009

Related U.S. Application Data

(63) Continuation of application No. 10/672,457, filed on Sep. 26, 2003, now Pat. No. 7,435,248.

(51) Int. Cl.
*A61B 18/14* (2006.01)
*A61B 5/042* (2006.01)

(52) U.S. Cl. ............ 606/41; 600/374; 600/381
(58) Field of Classification Search ......... 606/41
See application file for complete search history.

(56) References Cited

U.S. PATENT DOCUMENTS

| | | | |
|---|---|---|---|
| 4,650,466 A | 3/1987 | Luther | |
| 4,706,671 A | 11/1987 | Weinrib | |
| 4,921,484 A | 5/1990 | Hillstead | |
| 5,156,151 A | 10/1992 | Imran | |
| 5,228,442 A | 7/1993 | Imran | |
| 5,239,999 A | 8/1993 | Imran | |
| 5,263,493 A | 11/1993 | Avitall | |
| 5,279,299 A | 1/1994 | Imran | |
| 5,327,885 A | 7/1994 | Griffith | |
| 5,368,567 A | 11/1994 | Lee | |
| 5,383,874 A | 1/1995 | Jackson et al. | |
| 5,411,546 A | 5/1995 | Bowald et al. | |
| 5,456,667 A | 10/1995 | Ham et al. | |
| 5,456,682 A | 10/1995 | Edwards et al. | |
| 5,505,730 A | 4/1996 | Edwards | |
| 5,549,109 A | 8/1996 | Samson et al. | |

(Continued)

FOREIGN PATENT DOCUMENTS
EP 1 042 990 A1 10/2000
(Continued)

OTHER PUBLICATIONS

PCT International Search Report for PCT/US2004/030730, Applicant: Scimed Life Systems, Inc., Forms PCT/ISA/210 and 220, dated Feb. 18, 2005 (6 pages).

(Continued)

*Primary Examiner* — Lee S Cohen
(74) *Attorney, Agent, or Firm* — Vista IP Law Group LLP (57) ABSTRACT

The present inventions provide assemblies, probes, and methods for creating circumferential lesions in tissue, e.g., the tissue within or around the ostium of a vessel. An ablation probe with an ablative structure can be placed in contact within or around the ostium of the vessel. A diagnostic probe can be introduced through a lumen within the ablation probe and inserted into the vessel. The energy can be provided to the ablative structure to create a circumferential lesion within or around the ostium of the vessel, and the diagnostic structure can be used to diagnose the tissue to determine whether the circumferential lesion can be properly created.

19 Claims, 8 Drawing Sheets

U.S. PATENT DOCUMENTS

| | | | |
|---|---|---|---|
| 5,571,038 A | 11/1996 | Halling |
| 5,582,609 A | 12/1996 | Swanson et al. |
| 5,609,606 A | 3/1997 | O'Boyle |
| 5,680,860 A | 10/1997 | Imran |
| 5,702,368 A | 12/1997 | Stevens et al. |
| 5,733,280 A | 3/1998 | Avitall |
| 5,755,715 A | 5/1998 | Stern et al. |
| 5,797,905 A | 8/1998 | Fleischman et al. |
| 5,860,974 A | 1/1999 | Abele |
| 5,938,660 A | 8/1999 | Swartz et al. |
| 5,971,983 A | 10/1999 | Lesh |
| 5,972,019 A | 10/1999 | Engleson et al. |
| 5,991,650 A | 11/1999 | Swanson et al. |
| 6,012,457 A | 1/2000 | Lesh |
| 6,014,579 A | 1/2000 | Pomeranz et al. |
| 6,024,740 A | 2/2000 | Lesh et al. |
| 6,029,671 A | 2/2000 | Stevens et al. |
| 6,048,329 A | 4/2000 | Thompson et al. |
| 6,071,279 A | 6/2000 | Whayne et al. |
| 6,123,703 A | 9/2000 | Tu et al. |
| 6,142,994 A | 11/2000 | Swanson et al. |
| 6,164,283 A | 12/2000 | Lesh |
| 6,214,002 B1 | 4/2001 | Fleischman et al. |
| 6,251,109 B1 | 6/2001 | Hassett et al. |
| 6,287,301 B1 | 9/2001 | Thompson et al. |
| 6,311,692 B1 | 11/2001 | Vaska et al. |
| 6,325,797 B1 | 12/2001 | Stewart et al. |
| 6,383,151 B1 | 5/2002 | Diederich et al. |
| 6,416,511 B1 | 7/2002 | Lesh et al. |
| 6,464,700 B1 | 10/2002 | Koblish et al. |
| 6,485,489 B2 | 11/2002 | Teirstein et al. |
| 6,500,174 B1 | 12/2002 | Maguire et al. |
| 6,502,576 B1 | 1/2003 | Lesh |
| 6,503,247 B2 | 1/2003 | Swartz et al. |
| 6,514,249 B1 | 2/2003 | Maguire et al. |
| 6,527,769 B2 | 3/2003 | Langberg et al. |
| 6,529,756 B1 | 3/2003 | Phan et al. |
| 6,540,744 B2 | 4/2003 | Hassett et al. |
| 6,542,781 B1 | 4/2003 | Koblish et al. |
| 6,547,788 B1 | 4/2003 | Maguire et al. |
| 6,558,375 B1 | 5/2003 | Sinofsky et al. |
| 6,572,612 B2 | 6/2003 | Stewart et al. |
| 6,585,733 B2 | 7/2003 | Wellman |
| 6,645,199 B1 | 11/2003 | Jenkins et al. |
| 6,652,515 B1 | 11/2003 | Maguire et al. |
| 6,745,080 B2 | 6/2004 | Koblish |
| 6,771,996 B2 | 8/2004 | Bowe et al. |
| 6,923,808 B2 | 8/2005 | Taimisto |
| 2001/0007070 A1 | 7/2001 | Stewart et al. |
| 2001/0020174 A1 | 9/2001 | Koblish |
| 2002/0087208 A1 | 7/2002 | Koblish et al. |
| 2002/0111618 A1 | 8/2002 | Stewart et al. |
| 2003/0069570 A1 | 4/2003 | Witzel et al. |
| 2003/0078574 A1 | 4/2003 | Hall et al. |
| 2004/0024425 A1 | 2/2004 | Worley et al. |

FOREIGN PATENT DOCUMENTS

| | | |
|---|---|---|
| WO | WO 0137746 A1 | 5/2001 |
| WO | WO 03/022167 A1 | 3/2003 |
| WO | WO 03022167 A1 | 3/2003 |

OTHER PUBLICATIONS

PCT Written Opinion of the International Search Authority for PCT/US2004/030730, Application: Scimed Life Systems, Inc., Form PCT/ISA/237, dated Feb. 18, 2005 (6 pages).

PCT International Preliminary Report on Patentability (Chapter I of the Patent Cooperation Treaty) for PCT/US2004/030730, Application: Scimed Life Systems, Inc., Form PCT/IB/326, dated Apr. 6, 2006 (8 pages).

EPO Communication pursuant to Article 96(2) EPC issued by the European Patent Office for EP Patent Application No. 04 788 843.3-1526, Applicant: Boston Scientific Limited, dated May 31, 2007 (3 pages).

Office Communication issued by the Japanese Patent Office for JP Patent Application No. 2006-528088, Applicant: Boston Scientific Limited dated Apr. 21, 2010 (3 pages); English translation is prepared and provided by the Japanese associate Shusaku Yamamoto (4 pages).

EPO Communication pursuant to Article 94(3) EPC issued by the European Patent Office for EP Patent Application No. 04 788 843.3-1526, Applicant: Boston Scientific Limited dated Apr. 26, 2010 (5 pages).

MEDICAL PROBES FOR CREATING AND DIAGNOSING CIRCUMFERENTIAL LESIONS WITHIN OR AROUND THE OSTIUM OF A VESSEL

This application is a continuation of U.S. patent application Ser. No. 10/672,457, filed Sep. 26, 2003, now U.S. Pat. No. 7,435,248, the disclosure of which is hereby incorporated by reference.

FIELD OF THE INVENTION

The present inventions generally relate to medical ablation and diagnostic systems and methods, and more particularly to systems and methods for ablating and diagnosing tissue in and around orifices of vessels, such as pulmonary veins.

BACKGROUND OF THE INVENTION

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized manner to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

One surgical method of treating atrial fibrillation by interrupting pathways for reentry circuits is the so-called "maze procedure," which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery and is very expensive.

Maze-like procedures have also been developed utilizing catheters, which can form lesions on the endocardium (the lesions being 1 to 15 cm in length and of varying shape) to effectively create a maze for electrical conduction in a predetermined path. The formation of these lesions by soft tissue coagulation (also referred to as "ablation") can provide the same therapeutic benefits that the complex incision patterns that the surgical maze procedure presently provides, but without invasive, open heart surgery.

One lesion that has proven to be difficult to form with conventional devices is the circumferential lesion that is used to isolate the pulmonary vein and cure ectopic atrial fibrillation. Lesions that isolate the pulmonary vein may be formed within the pulmonary vein itself or in the tissue surrounding the pulmonary vein. Ablation of pulmonary veins is currently performed by placing a diagnostic catheter (such as Biosense Webster's Lasso™ circular ECG catheter, Irvine Biomedical's Afocus™ circular ECG catheter, or Boston Scientific Corporation's Constellation™ ECG catheter) into the pulmonary vein to be treated, and then ablating the pulmonary tissue adjacent to the distal end of the selected diagnostic catheter with a standard, commercially available ablation catheter. The diagnostic catheter is used to determine if the lesion created by the ablation catheter has been successful in electrically isolating the pulmonary vein.

Some physicians may alternatively use a standard linear diagnostic catheter with 2-20 ECG electrodes to evaluate pre-ablation electrocardiogram (ECG) recordings, then swap the diagnostic catheter with a standard ablation catheter either through the same sheath, or in conjunction with the ablation catheter through a second sheath, ablating the pulmonary tissue, and then swapping the ablation catheter with the diagnostic catheter to evaluate post-ablation ECG recordings.

In any event, the circumferential lesion must be iteratively formed by placing the ablation electrode into contact with a tissue region, ablating the tissue region, moving the ablation electrode into contact with another tissue region, and then ablating again. In a standard procedure, placement of the electrode and ablation of tissue may be repeated from 15-25 times to create the circumferential lesion. It is often difficult to form an effective circumferential lesion, however, by forming a pattern of relatively small diameter lesions. More recently, inflatable balloon-like devices that can be expanded within or adjacent to the pulmonary vein have been introduced. Although the balloon-like devices are generally useful for creating circumferential lesions, these devices have the undesirable effect of occluding blood flow through the pulmonary vein.

In response to these problems, a corkscrew-type ablation catheter has been recently designed. This catheter comprises a helical distal end on which a plurality of ablation electrodes are mounted. The helical distal end can be inserted into a pulmonary vein to be treated and operated to efficiently produce a circumferential lesion, while allowing passage of blood. The ablation electrodes on the corkscrew-type ablation catheter can also be used to generate ECG recordings as a frame of reference for the ablation procedure. In use, it has been noted that ECG drops in amplitude are an indicator of potential pulmonary vein electrical isolation. Although this technique has proven successful, the ablation device does not offer as high of an ECG signal resolution as would a dedicated ECG catheter.

Accordingly, there remains a need to be able to more efficiently create circumferential lesions and provide high resolution ECG recordings within or around bodily orifices without occluding fluid flow and, in the context of the treatment of atrial fibrillation, within or around the pulmonary vein without occluding blood flow.

SUMMARY OF THE INVENTION

In accordance with a first aspect of the present invention, a probe for ablating tissue, e.g., the tissue within a pulmonary vein, is provided. The probe comprises an outer elongate probe body (e.g., an intravascular catheter body or a surgical probe body) including a distal ablative structure having an open architecture defining an interior space. For example, the distal ablative structure can be a loop structure or an open helical structure. The probe further comprises a lumen extending through the outer probe body. The lumen is configured to slidably receive an inner elongate probe body, and comprises an exit port out which the inner probe body can extend within the interior space of the ablative structure. The probe further comprises one or more ablative elements mounted to the distal ablative structure, wherein the one or more ablative elements are arranged to create a circumferential lesion. For example, the ablative structure of the outer probe body can be configured to be disposed within or around the ostium of a pulmonary vein, in which case, the ablative element(s) can be configured to circumferential contact tissue within or around the ostium of the pulmonary vein.

In accordance with a second aspect of the present invention, a probe assembly for ablating tissue is provided. The probe assembly comprises an outer probe body that includes an ablative structure, e.g., a loop structure, open helical structure, or expandable balloon. The probe assembly further comprises an inner probe configured to be slidably disposed within the lumen of the outer probe. The inner probe includes an elongate probe body having a distal diagnostic structure configured to extend out the exit port, and one or more diagnostic elements (e.g., electrophysiology mapping elements) mounted to the distal diagnostic structure. The diagnostic structure may be formed of a single spline to provide a low profile, or some other structure, such as a basket structure. In one preferred embodiment, the diagnostic structure is configured to assume an curvilinear shape in order to provide a firm and stable contact between the diagnostic elements and the tissue.

In accordance with a third aspect of the present inventions, a method of creating a circumferential lesion adjacent an anatomical vessel, such as a pulmonary vein, is provided. The method comprises placing an ablation probe within or around an ostium of the vessel, and circumferentially arranging one or more ablative elements carried by the ablation probe within or around the ostium of the vessel. The method further comprises inserting a diagnostic probe within the vessel, wherein the diagnostic probe is disposed within the vessel while the ablation probe is placed within or around the ostium of the vessel. The diagnostic probe can be, e.g., introduced through a lumen within the ablation probe.

The method further comprises creating a circumferential lesion within or around the ostium of the vessel by energizing the ablative element(s). For example, radio frequency (RF) can be provided to the ablation element(s). Other forms of energy, such as chemical, laser, microwave, etc., can also be provided. In the case where the vessel is a pulmonary vein, the circumferential lesion will advantageously electrically isolate the pulmonary vein from the left atrium of the heart. In a preferred method, the circumferential lesion is created without moving the ablative elements within the vessel, thereby efficiently and quickly performing the ablation process. In one preferred method, fluid, such as, e.g., blood, is allowed to flow through the vessel while the circumferential lesion is created.

The method further comprises measuring diagnostic signals within the vessel with the diagnostic probe. In the case where the vessel is a pulmonary vein, the diagnostic signals can be electrocardiogram (ECG) signals. In one preferred method, the diagnostic signals are measured subsequent to the creation of the circumferential lesion, e.g., to determine whether the circumferential lesion has been properly formed. The diagnostic signals can also be measured prior to or during the creation of the circumferential lesion.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

The embodiments disclosed herein may be used within body lumens, chambers or cavities for diagnostic or therapeutic purposes in those instances where access to interior bodily regions is obtained through, for example, the vascular system or alimentary canal and without complex invasive surgical procedures. For example, the embodiments herein have application in the diagnosis and treatment of arrhythmia conditions within the heart. The embodiments herein also have application in the diagnosis or treatment of ailments of the gastrointestinal tract, prostrate, brain, gall bladder, uterus, and other regions of the body.

With regard to the treatment of conditions within the heart, the embodiments herein are designed to produce intimate tissue contact with target substrates associated with various arrhythmias, namely atrial fibrillation, atrial flutter, and ventricular tachycardia. For example, the distal portion of a catheter used in the embodiments herein can be used to create lesions within or around the pulmonary vein to treat ectopic atrial fibrillation.

Although the embodiments illustrated herein are catheter-based, the embodiments are adaptable for use with probes other than catheter-based probes. For example, the structures disclosed herein may be used in conjunction with hand held surgical devices (or "surgical probes"). The distal end of a surgical probe may be placed directly in contact with the targeted tissue area by a physician during a surgical procedure, such as open heart surgery. Here, access may be obtained by way of a thoracotomy, median sternotomy, or thoracostomy. Exemplary surgical probes are disclosed in U.S. Pat. No. 6,142,994, which is expressly incorporated herein by reference.

Figure 1:
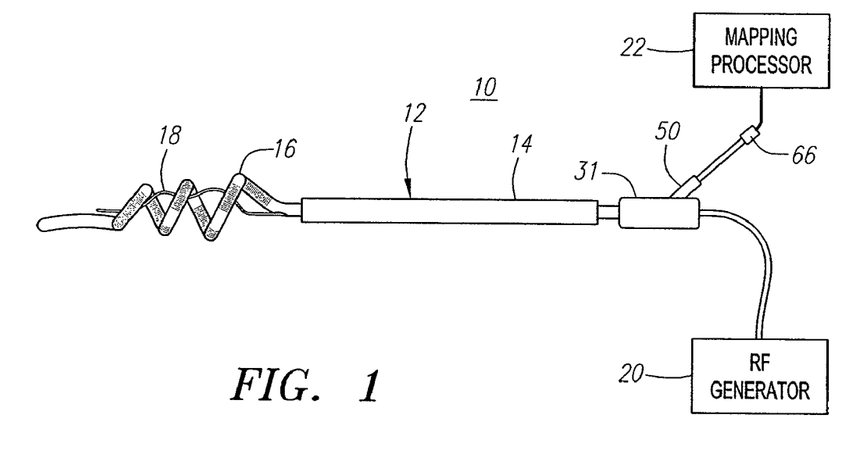
FIG. 1 is a plan view of one preferred embodiment of a medical treatment system constructed in accordance with the present inventions.

Referring to FIG. 1, an exemplary ablation/diagnostic system 10 constructed in accordance with the present inventions is shown. The system 10 may be used within body lumens, chambers or cavities for diagnostic or therapeutic purposes in those instances where access to interior bodily regions is obtained through, for example, the vascular system or alimentary canal and without complex invasive surgical procedures. For example, the system 10 has application in the diagnosis and treatment of arrhythmia conditions within the heart. The system 10 also has application in the diagnosis or treatment of ailments of the gastrointestinal tract, prostrate, brain, gall bladder, uterus, and other regions of the body. As an example, the system 10 will be described hereinafter for use in pulmonary veins, and specifically, to electrically isolate a pulmonary vein from the left atrium of the heart in order to treat ectopic atrial fibrillation.

The system 10 generally comprises an ablation/diagnostic catheter assembly 12, which includes a guide sheath 14, an ablation catheter 16 that can be guided through the guide sheath 14, and a diagnostic catheter, and specifically, a mapping catheter 18, integrated within the ablation catheter 16. As will be described in further detail below, the catheter assembly 12 is configured to be introduced through the vasculature of the patient, and into the left atrium of the heart, where it can be used to map and ablate the tissue within and around a selected pulmonary vein. The treatment system 10 further comprises an ablation source, and specifically, a radio frequency (RF) generator 20, and an mapping processor 22.

The mapping processor 22 is configured to record and process ECG signals obtained from the mapping catheter 18 to determine irregular electrical signals within the heart, and specifically electrical signals adjacent the ostia of the pulmonary veins. Recording ECG signals is well known in the art, and thus for purposes of brevity, the mapping processor 22 will not be described in further detail. The RF generator 20 is configured to deliver ablation energy to the ablation catheter 16 in a controlled manner in order to ablate the area around the ostium of the pulmonary vein identified by the mapping processor 22. Alternatively, other types of ablative sources besides the RF generator 20 can be used, e.g., a microwave generator, an ultrasound generator, a cryoablation generator, and a laser or other optical generator. Ablation of tissue within the heart is well known in the art, and thus for purposes of brevity, the RF generator 20 will not be described in further detail. Further details regarding RF generators are provided in U.S. Pat. No. 5,383,874, which is expressly incorporated herein by reference.

The ablation catheter 16 is not a steerable catheter and, accordingly, may be advanced though the conventional steerable guide sheath 14 to the target location. The sheath 14, which should be lubricious to reduce friction during movement of the ablation catheter 16, may be advanced over a guidewire in conventional fashion. Alternatively, a steerable sheath may be provided. With respect to materials, the proximal portion of the sheath 14 is preferably a Pebax® material and stainless steel braid composite, and the distal portion is a more flexible material, such as unbraided Pebax®, for steering purposes. The sheath 14 should also be stiffer than the ablation catheter 16. A sheath introducer (not shown), such as those used in combination with basket catheters, may be used when introducing the ablation catheter 16 into the sheath 14. The guide sheath 14 preferably includes a radio-opaque compound, such as barium, so that the guide sheath 14 can be observed using fluoroscopic or ultrasound imaging, or the like. Alternatively, a radio-opaque marker (not shown) can be placed at the distal end of the guide sheath 14.

Figure 2:
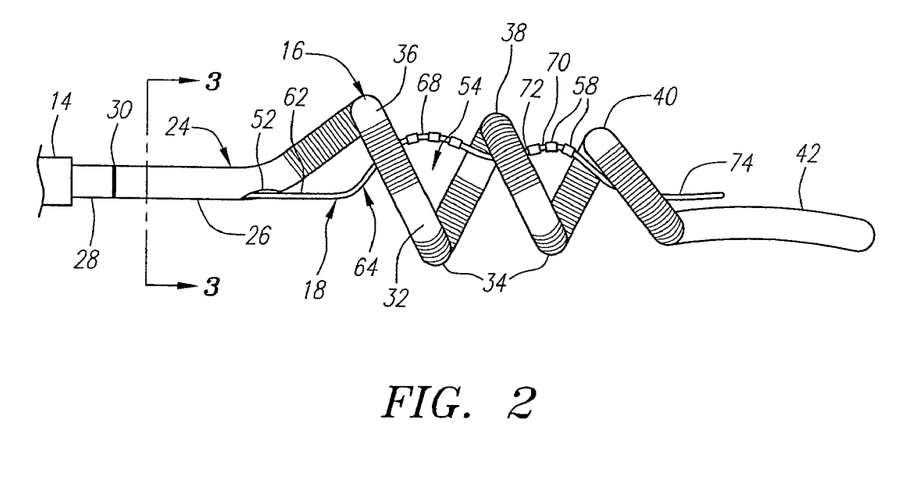
FIG. 2 is a plan view of an ablation/mapping catheter assembly that can be used in the medical treatment system of FIG. 1.

Referring now to FIG. 2, the ablation catheter 16 comprises a flexible catheter body 24 formed of a proximal member 28 and a distal member 26. The proximal member 26 is relatively long (e.g., 80-100 cm) while the distal member 26 is relatively short (e.g., 2-10 cm). The proximal member 26 is preferably formed from a biocompatible thermoplastic material, such as a Pebax® material (polyether block amide) and stainless steel braid composite, which has good torque transmission properties. In some implementations, an elongate guide coil (not shown) may also be provided within the proximal member 26. A handle assembly 31 (shown in FIG. 1) is mounted to the proximal end of the proximal member 26. The distal member 26 is preferably formed from a softer, more flexible biocompatible thermoplastic material such as unbraided Pebax® material, polyethylene, or polyurethane. The proximal and distal members, which are about 5 French to about 9 French in diameter, are preferably either bonded together at interface 30 with an overlapping thermal bond or adhesively bonded together end to end over a sleeve in what is referred to as a "butt bond."

The distal member 26 of the ablation catheter body 24 forms an unconstrained open helically-shaped ablative structure 32 on which ablation electrodes 34 are mounted. The ablative structure 32 defines a longitudinal axis coincident with the longitudinal axis of the remainder of the catheter body 24. The number of revolutions (or "coils"), length, diameter, orientation and shape of the helical structure will vary from application to application. In the illustrated embodiment, the ablative structure 32 revolves around the longitudinal axis of the catheter body 24 two and one-half times in its relaxed state, and can be defined with a proximal coil 36, medial coil 38, and distal coil 40.

Although the diameter of the ablative structure 32 can alternatively be substantially constant over its length, as illustrated in FIG. 2, the ablative structure 32 preferably has a generally frusto-conical shape, where the diameter decreases in the distal direction. Specifically, when used in pulmonary veins, the proximal coil 36 of the ablative structure 32 preferably has an outer diameter that will cause it abut the pulmonary vein ostium (e.g., between about 15 mm and about 35 mm), and the distal coil 40 of the ablative structure 32 preferably has an outer diameter suitable for placement within the pulmonary vein (e.g., between about 5 mm and about 10 mm). The ablative structure 32 will, therefore, be self-centering when inserted into the pulmonary vein, because the tapered ablative structure 32 will wedge itself against the pulmonary vein ostium and the internal wall of pulmonary vein itself. Not only does this result in proper positioning of the electrodes 34, the wedging effect also prevents beating related movement of the heart from the knocking the ablation catheter 16 out of position once it is in place.

The distal member 26 of the catheter body 24 also forms a distal anchoring structure 42, which allows the ablative structure 32 to be precisely located relative to the pulmonary vein. More specifically, advancing the anchoring structure 42 into the pulmonary vein aligns the ablative structure 32 with the pulmonary vein. In the illustrated embodiment, the anchoring structure 42 is simply the portion of the distal member 26 that is distal to the ablative structure 32. Alternatively, a separate structure may be secured to the distal end of the distal member 26. The exemplary anchoring structure 42 is approximately 1 to 2 inches in length, although other lengths may be used to suit particular applications.

Figure 3:
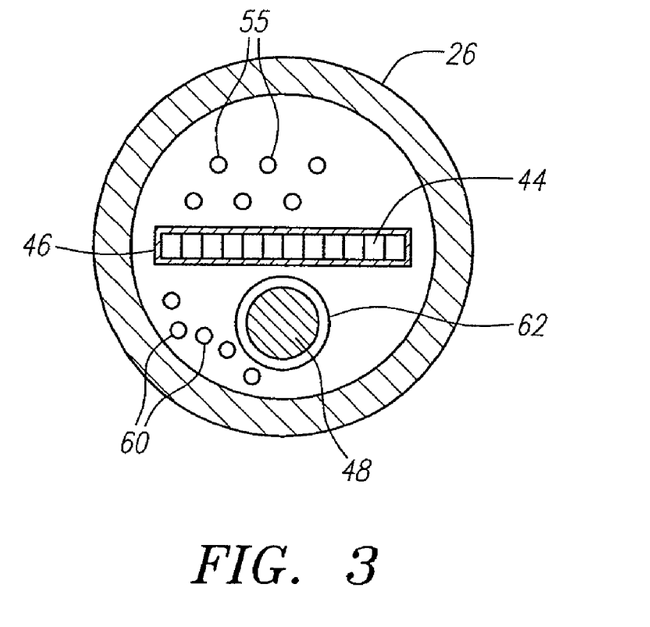
FIG. 3 is a cross-sectional view of the catheter assembly of FIG. 2, taken along the lines 3-3.

Referring to FIG. 3, the shape of the ablative structure 32 is achieved through the use of a center support 44 that is positioned inside of and passes within the length of the distal member 26. In the illustrated embodiment, the center support 44 is a rectangular wire formed from resilient inert wire, such as Nickel Titanium (commercially available under the trade name Nitinol) or 17-7 stainless steel wire, with a portion thereof heat set into the desired helical configuration. Alternatively, the center support 44 can be circular. The thickness of the rectangular center support 44 is preferably between about 0.010 inch and about 0.015 inch. Resilient injection molded plastic can also be used. Although other cross sectional configurations can be used, such as a round wire, a rectangular cross section arranged such that the longer edge extends in the longitudinal direction is preferred for at least the ablative structure 32.

Such an orientation reduces the amount of torsional force, as compared to a round wire, required to unwind the ablative structure 32 into an expanded configuration and collapse the ablative structure 32 into a linear structure. The center support 44 is preferably housed in an insulative tube 46 formed from material such as Teflon®. or polyester. Additional details concerning the placement of a center support within the distal member of a catheter can be found in commonly assigned U.S. patent application Ser. No. 09/150,833, entitled "Catheter Having Improved Torque Transmission Capability and Method of Making the Same," which is expressly incorporated herein by reference.

Preferably, the distal portion of the distal member 26 is more flexible than the proximal portion of the distal member 26 in order to prevent tissue damage when attempts are made to insert the ablative structure 32 into a pulmonary vein. In addition, the ablative structure 32 will be more predisposed to easily uncoil for placement within the sheath 14, remain uncoiled and slide though the sheath 14 until it exits through the distal end of the sheath and re-coils, and then easily uncoil again when pulled back into the sheath after the procedure is completed. Also, the stiffer proximal portion of the distal member 26 allows the physician to press the ablation electrodes 34 against the tissue with more force when lesions are being created. The flexibility of the distal portion of the distal member 26 can be increased in variety of ways, e.g., by using a core wire (not shown) having a varying stiffness, or by constructing the distal member 26 from different materials. Further details on the construction of helical structures with varying flexibility are disclosed in U.S. patent application Ser. No. 09/832,612, entitled "Helical and Pre-Oriented Loop Structures for Supporting Diagnostic and Therapeutic Elements in Contact with Body Tissue," which is expressly incorporated herein by reference.

The ablation catheter 16 may comprise an optional stylet (not shown) that enables the physician to manipulate the ablative structure 32 and adjust its shape by longitudinally and/or rotating the stylet. Further details on the construction and use of the stilette, along with a handle assembly specifically designed to manipulate the stilette, are disclosed in U.S. patent application Ser. No. 09/832,612.

The ablation catheter 16 comprises a lumen 48 (in addition to other lumens for providing ablation and signals wires described below) for slidably receiving the mapping catheter 18 (shown in FIG. 2). The lumen 48 proximally terminates in the handle assembly 31 at an insertion port 50 (shown in FIG. 1) and distally terminates in the distal member 26 at an exit port 52 (shown in FIG. 2) just proximal to the ablative structure 32. Thus, the mapping catheter 18 can be introduced into the insertion port 50 on the handle assembly 31, through the lumen 48, and out the exit port 52, so that it extends within an interior space 54 created by the ablative structure 32.

The spaced ablation electrodes 34 are preferably in the form of wound, spiral coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. A preferred coil electrode is disclosed in U.S. Pat. No. 5,797,905, which is expressly incorporated herein by reference. The electrodes 34 are electrically coupled to individual wires 55 (shown in FIG. 3) to conduct coagulating energy to them. The wires are passed in conventional fashion through a lumen extending through the associated catheter body into a PC board (not shown) in the handle assembly 31, where they are electrically coupled to a connector (not shown) that is received in a port on the handle assembly 31. The connector plugs into the RF generator 20 (shown in FIG. 1).

As an alternative, the ablation electrodes 34 may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel or titanium can be applied. The electrodes 34 can also be in the form of helical ribbons. The electrodes 34 can also be formed with a conductive ink compound that is pad printed onto a nonconductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes 34. Such inks are more flexible than epoxy-based inks.

The flexible electrodes 34 are preferably about 4 mm to about 20 mm in length. In the preferred embodiment, the electrodes are 12.5 mm in length with 1 mm to 3 mm spacing, which will result in the creation of continuous lesion patterns in tissue when coagulation energy is applied simultaneously to adjacent electrodes 34. For rigid electrodes 34, the length of the each electrode can vary from about 2 mm to about 10 mm. Using multiple rigid electrodes 34 longer than about 10 mm each adversely effects the overall flexibility of the device, while electrodes 34 having lengths of less than about 2 mm do not consistently form the desired continuous lesion patterns.

The portion of the electrodes 34 that are not intended to contact tissue (and be exposed to the blood pool) may be masked through a variety of techniques with a material that is preferably electrically and thermally insulating. This prevents the transmission of coagulation energy directly into the blood pool and directs the energy directly toward and into the tissue. For example, a layer of UV adhesive (or another adhesive) may be painted on preselected portions of the electrodes 34 to insulate the portions of the electrodes not intended to contact tissue. Deposition techniques may also be implemented to position a conductive surface only on those portions of the assembly intended to contact tissue. Alternatively, a coating may be formed by dipping the electrodes 34 in PTFE material.

The electrodes 34 can include a porous material coating, which transmits coagulation energy through an electrified ionic medium. For example, as disclosed in U.S. Pat. No. 5,991,650, electrodes 34 may be coated with regenerated cellulose, hydrogel or plastic having electrically conductive components. With respect to regenerated cellulose, the coating acts as a mechanical barrier between the surgical device components, such as electrodes, preventing ingress of blood cells, infectious agents, such as viruses and bacteria, and large biological molecules such as proteins, while providing electrical contact to the human body. The regenerated cellulose coating also acts as a biocompatible barrier between the device components and the human body, whereby the components can now be made from materials that are somewhat toxic (such as silver or copper).

The electrodes 34 may be operated in a uni-polar mode, in which the soft tissue coagulation energy emitted by the electrodes 34 is returned through an indifferent patch electrode (not shown) externally attached to the skin of the patient. Alternatively, the electrodes 34 may be operated in a bi-polar mode, in which energy emitted by one or more electrodes 34 is returned through other electrodes 34. The amount of power required to coagulate tissue ranges from 5 to 150 W.

Although ablation electrodes 34 have been described as the operative elements that create the lesion, other operative elements, such as lumens for chemical ablation, laser arrays, ultrasonic transducers, microwave electrodes, and ohmically heated hot wires, and such devices may be substituted for the electrodes 34.

The ablation catheter 16 further comprises temperature sensors (not shown), such as thermocouples or thermistors, which may be located on, under, abutting the longitudinal end edges of, or in between, the electrodes 34. Preferably, the temperature sensors are located at the longitudinal edges of the electrodes 34 on the distally facing side of the ablative structure 32. In some embodiments, a reference thermocouple (not shown) may also be provided. For temperature control purposes, signals from the temperature sensors are transmitted to the source of coagulation energy by way of wires 60 (shown in FIG. 3) that are also connected to the aforementioned PC board in the handle assembly 31. Suitable temperature sensors and controllers which control power to electrodes based on a sensed temperature are disclosed in U.S. Pat. Nos. 5,456,682, 5,582,609 and 5,755,715.

The mapping catheter 18 comprises a flexible catheter body 62 formed of a flexible spline composed of a resilient, biologically inert material, like Nitinol metal or silicone rubber. Thus, the mapping catheter body 62 is configured to bend and conform to the endocardial and pulmonary vein tissue surface its contacts. In the illustrated embodiment, the diameter of the mapping catheter body 62 is relatively small (e.g., 3-4 F), so that the ablation catheter 16 that houses the mapping catheter 18 assumes a small profile.

The distal end of the mapping catheter body 62 forms a mapping structure 64. The mapping catheter 18 comprises mapping electrodes 58 extending along the mapping structure 64. In the illustrated embodiment, the mapping electrodes 58 are ring electrodes that are composed of a solid, electrically conducting material, like platinum or gold, attached about the catheter body 62. Alternatively, the mapping electrodes 58 can be formed by coating the exterior surface of the catheter body 62 with an electrically conducting material, like platinum or gold. The coating can be applied using sputtering, ion beam deposition, or equivalent techniques. The mapping electrodes 58 can have suitable lengths, such as between 0.5 and 5 mm.

In use, the mapping electrodes 58 sense electrical events in myocardial tissue for the creation of electrograms, and are electrically coupled to the mapping processor 22 (see FIG. 1). A signal wire (not shown) is electrically coupled to each mapping electrode 58. The wires extend through the catheter body 62 into an external multiple pin connector 66. The connector 66 electrically couples the mapping electrodes 58 to the mapping processor 22.

As illustrated in FIG. 2, the mapping structure 64 extends distally within an interior space 54 of the ablative structure 32, and is curved in an undulated fashion that will resiliently place the mapping electrodes 58 in contact with the tissue of the vessel in which the ablation and mapping catheters 16 and 18 are placed. Specifically, the total transverse distance that the mapping structure 64 curves is greater than the diameter of the selected vessel, so that placement of the mapping structure 64 within the vessel will cause the vessel wall to provide a compressive force mapping structure 64, thereby resiliently lodging the mapping structure 64 within the vessel.

In the illustrated embodiment, the mapping structure 64 comprises first and second curved sections 68 and 70 having apexes that point in the same direction away from the longitudinal axis of the ablation catheter 16, and an mediate curved section 72 between the proximal and distal curved sections 68 and 70 having an apex that points towards the longitudinal axis of the ablation catheter 16. In this manner, when the mapping structure 64 is deployed from the exit port 52 of the ablation catheter lumen 48, the proximal curved section 68 may come in contact with tissue between the proximal and medial coils 36 and 38 of the ablative structure 32, and the distal curved section 70 may come in contact with tissue between the mediate and distal coils 38 and 40 of the ablative structure 32. The medial curved section 72 provides clearance between the mapping structure 64 and the medial coil 38 of the ablative structure 32.

The distal end of the mapping catheter body 62 further forms a straight distal section 74 that is configured to stabilize the mapping structure 64 by contacting the portion of the vessel wall opposite the portion in which the proximal and distal curved sections 68 and 70 contact. Preferably, the distal section 74 is floppy, similar to the tip of a guidewire, thereby minimizing tissue trauma.

It should be noted that although the mapping catheter body 62 has been described as a linear resilient spline, the catheter body 62 can also have other shapes, such as, e.g., a spiral, basket, etc., that allow the mapping catheter body 62 to collapse into the lumen 48 of the ablation catheter body 62.

Having described the structure of the treatment system 10, its operation in creating a circumferential lesion within the ostium of a pulmonary vein, thereby electrically isolating it from the left atrium of the heart, will now be described with reference to FIGS. 4-6. It should be noted that the views of the heart 200 and other interior regions of the body described herein are not intended to be anatomically accurate in every detail. The Figures show anatomic details in diagrammatic form as necessary to show the features of the embodiment described herein.

Figure 4:
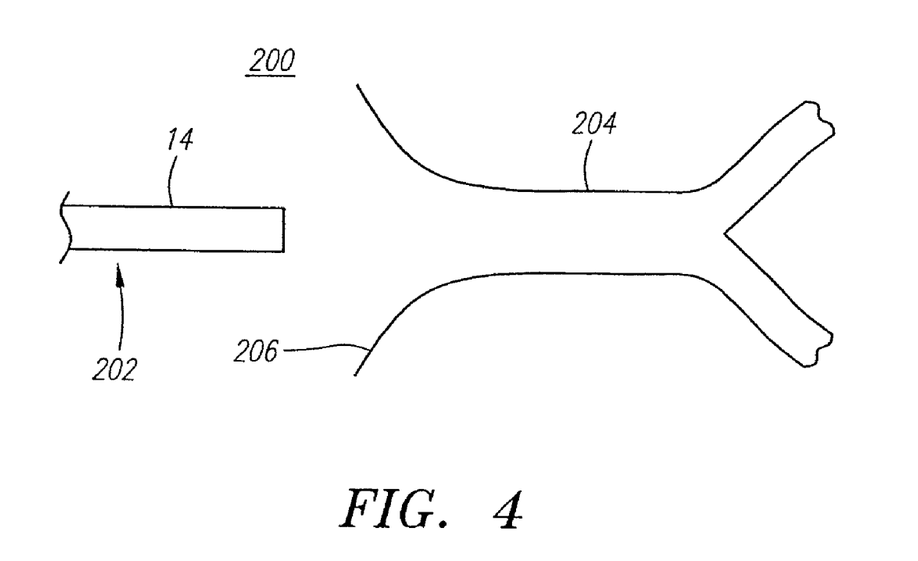
FIGS. 4-6 are plan views of a method of using the catheter assembly of FIG. 2 to create a circumferential lesion within the ostium of a pulmonary vein.

Referring specifically to FIG. 4, the guide sheath 14 is introduced into the left atrium 202 of the heart 200, so that the distal end of the sheath 14 is adjacent a selected pulmonary vein 204. Introduction of the guide sheath 14 within the left atrium 202 can be accomplished using a conventional vascular introducer retrograde through the aortic and mitral valves, or can use a transeptal approach from the right atrium. A guide catheter or guide wire (not shown) may be used in association with the guide sheath 14 to aid in directing the guide sheath 14 through the appropriate artery toward the heart 200.

Once the distal end of the guide sheath 14 is properly placed, the ablation catheter 16 is introduced through the guide sheath 14 until the ablative structure 32 is deployed from the guide sheath 14. The ablation catheter 16 is then manipulated, so that the anchoring structure 42, and then the ablative structure 32, is placed inside the ostium 206 of the pulmonary vein 204, as illustrated in FIG. 5. The resiliency of the ablative structure 32 places the ablation electrodes 34 in firm and stable contact with the wall of the pulmonary vein 204. For purposes of illustration, the ablative structure 32 is shown disposed well within the pulmonary vein 24. In practice, however, the entire ablative structure 32 will engage the portion of the pulmonary vein 204 just distal to the ostium 206. The mapping catheter 18 is then introduced into the entry port 50 on the handle assembly 31, through the lumen 48 of the ablation catheter 16 until the mapping structure 64 is deployed out from the exit port 52 into the interior space 54 formed by the ablative structure 32. Introduction of the mapping catheter 18 within the lumen 48 of the ablation catheter 16 can either be accomplished prior to or subsequent to the introduction of the ablation catheter 16 within the left atrium 202 of the heart 200.

Figure 5:
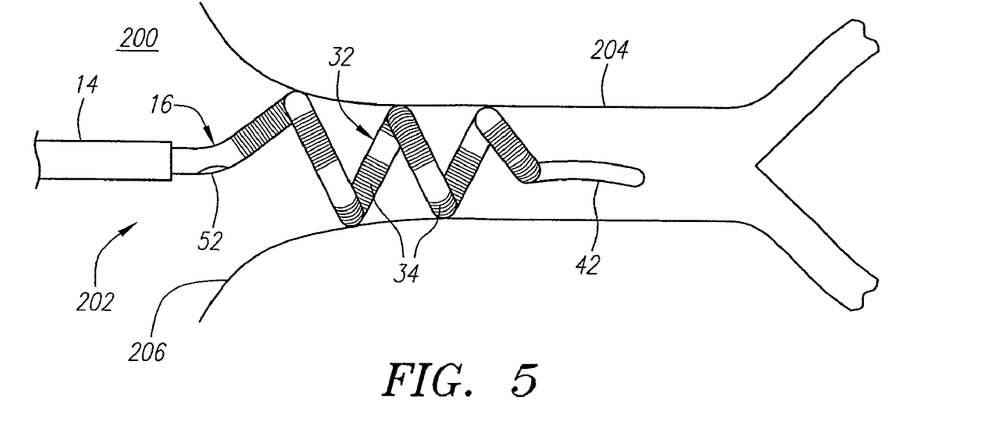
Figure 6:
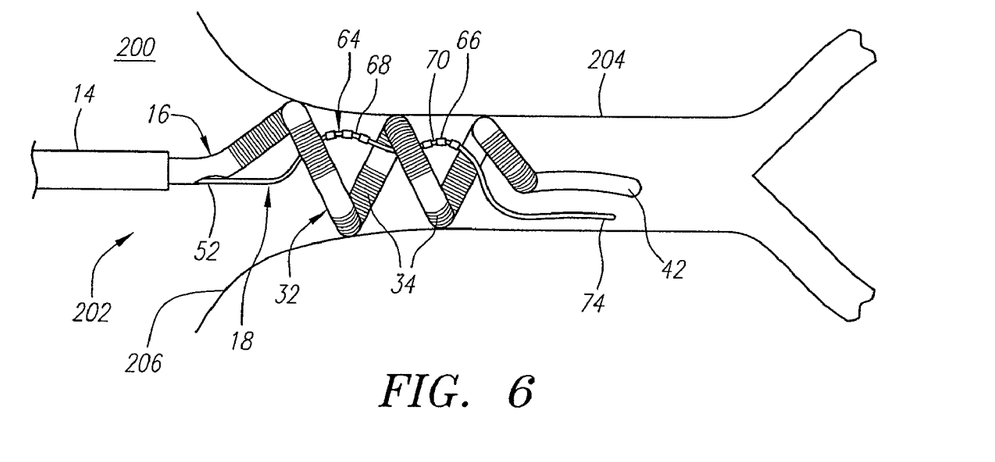

As illustrated in FIG. 5, the mapping structure 64 is placed firmly in contact with the tissue inside the pulmonary vein 204. Specifically, the proximal and medial curved sections 68 and 70 of the mapping structure 64 are isolaterally in contact along the wall of the pulmonary vein 204, and the distal straight section 74 is contralaterally in contact along the wall of the pulmonary vein 204. As a result, the electrodes 58 of the mapping structure 64 will be firmly and stably in contact with the tissue. Once this electrode contact has been achieved, the mapping processor 22 is operated in order to obtain and record ECG signals from the pulmonary vein tissue. As described below, these ECG signals will be compared with the ECG signals obtained subsequent to an ablation procedure in order to determine if the resultant lesion has successfully electrically isolated the pulmonary vein 204 from the left atrium 202 of the heart 200.

One the pre-ablation ECG signals have been obtained and recorded, the RF generator 20 is operated in order to convey RF energy to the ablation electrodes 34. In the illustrated embodiment, the RF energy is conveyed to the electrodes 34 one at a time. Thus, assuming that there are six ablation electrodes 34, six ablation procedures are performed in order to create a circumferential lesion around the wall of the pulmonary vein 204. Alternatively, the RF energy is simultaneously conveyed to all six electrodes 34. In this manner, a single ablation procedure is performed in order to create the circumferential lesion. In either case, the ablation electrodes 34 need not be moved during the ablation procedure(s).

After the lesion has been created, the mapping processor 22 is again operated to obtain and record ECG signals from the pulmonary vein 204. These post-ablation ECG signals are compared to the pre-ablation ECG signals to determine whether the circumferential lesion has completely isolated the pulmonary vein 204 from the left atrium 202 of the heart 200. The mapping structure 64 can be rotated or otherwise moved in order to obtain and record ECG signals on other regions of the pulmonary vein 204. Once proper ablation has been confirmed, the guide sheath 14, ablation catheter 16, and mapping catheter 18 are removed from the patient's body, or alternatively, are used to create a circumferential lesion within another pulmonary vein.

Figure 7:
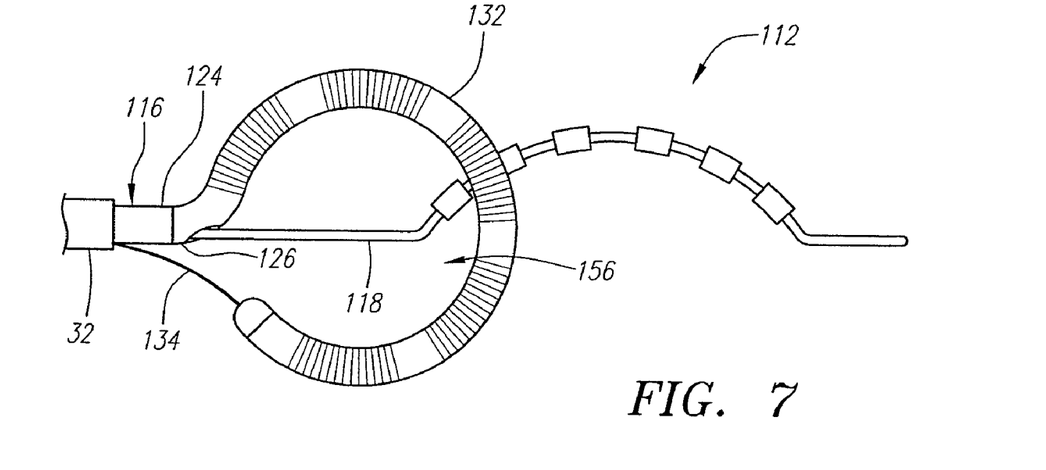
FIG. 7 is a plan view of another ablation/mapping catheter assembly that can be used in the medical treatment system of FIG. 1.

Referring now to FIG. 7, an alternative embodiment of a catheter assembly 112 that can be used in the treatment system 10 of FIG. 1 is shown. The catheter assembly 112 is similar to the previously described catheter assembly 12, with the exception that the ablation catheter body forms a loop-shaped, rather than a helically-shaped, ablative structure. Specifically, an ablation catheter 116 comprises a flexible elongate catheter body 124 having a distal member 126 that forms a loop-shaped ablative structure 132. The ablation catheter 116 further comprises a pull wire 134, which extends from the tip of the distal member 126 back through the sheath 32. The pull wire 134 is used to pull the distal member 116 into a loop configuration. The pull wire 134 also maintains the shape of the ablative structure 132 (thereby insuring good tissue contact) when the loop structure 132 is urged against tissue, such as a pulmonary vein ostium.

Figure 8:
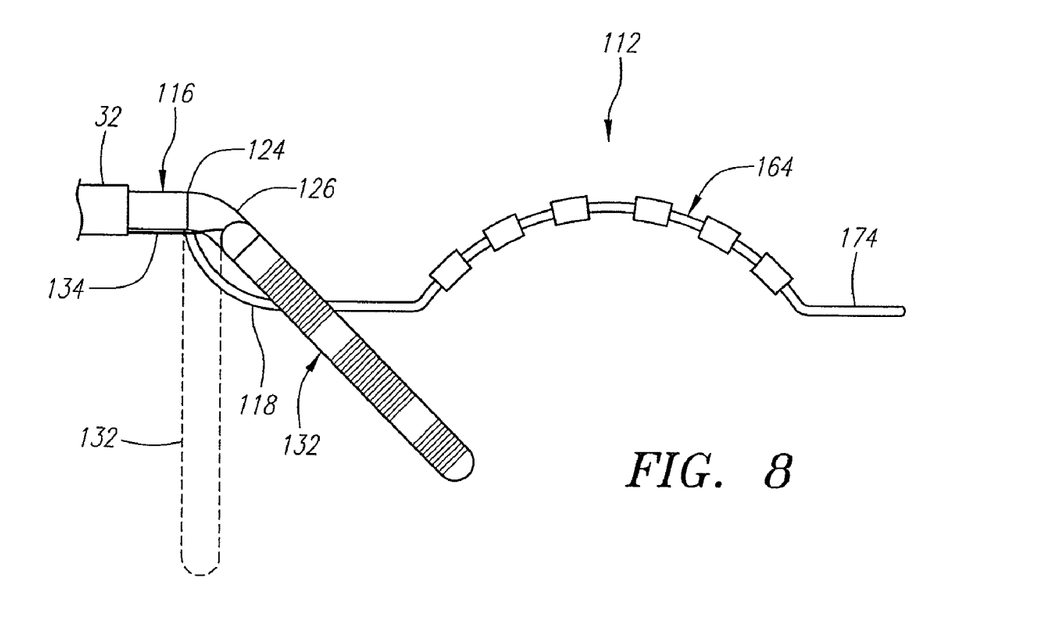
FIG. 8 is a profile view of the catheter assembly of FIG. 7.

In the illustrated embodiment, the ablative structure 132 forms a curved portion with a radius of about 0.5 inch. The curved portion lies in a plane between about 30 and about 60 degrees, and preferably about 45 degrees, out of the horizontal catheter plane, as illustrated in FIG. 8. The preset curvature may be accomplished in a variety of ways. Preferably, the curved portion is preset through the use of a thermal forming technique (100° C. for 1 hour). The preset curvature may also be accomplished through the use of a pre-shaped core wire (not shown) formed from Nitinol or 17-7 stainless steel. The curved portion will typically be bent out of its pre-bent orientation when the ablative structure 132 is urged against tissue (note the dashed lines in FIG. 8). As a result, a spring force that urges the ablative structure 132 against the tissue is generated, thereby improving tissue/electrode contact.

The pull wire 134 is preferably a flexible, inert cable constructed from strands of metal wire material, such as Nitinol or 17-7 stainless steel, that is about 0.012 inch to about 0.025 inch in diameter. Alternatively, the pull wire 134 may be formed from a flexible, inert stranded or molded plastic material. The pull wire 134 is also preferably round in cross-section, although other cross-sectional configurations can be used. Further details on the construction of loop-shaped ablative structures and pull wires are disclosed in U.S. patent application Ser. No. 09/832,612, which has previously been incorporated herein by reference, and U.S. Pat. No. 6,048,329, which is expressly incorporated herein by reference.

The catheter assembly 112 further comprises a mapping catheter 118 that includes a catheter body 164 with a mapping structure 164 that extends distally through an interior space 156 of the ablative structure 132. The mapping structure 164 is similar to the previously described mapping structure 64, with the exception that is forms a single curve that will extend along one side of the pulmonary vein contralaterally to a straight distal section 174.

Figure 9:
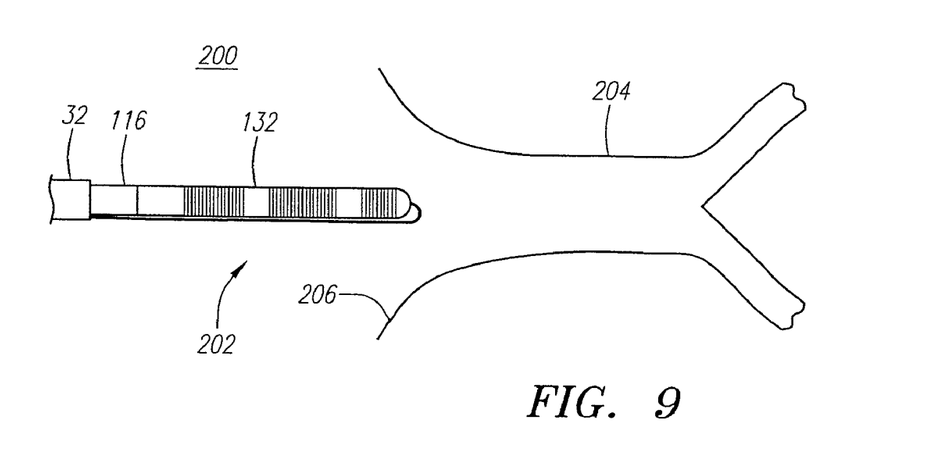
FIGS. 9-11 are plan views of a method of using the catheter assembly of FIG. 7 to create a circumferential lesion around the ostium of a pulmonary vein.
Figure 10:
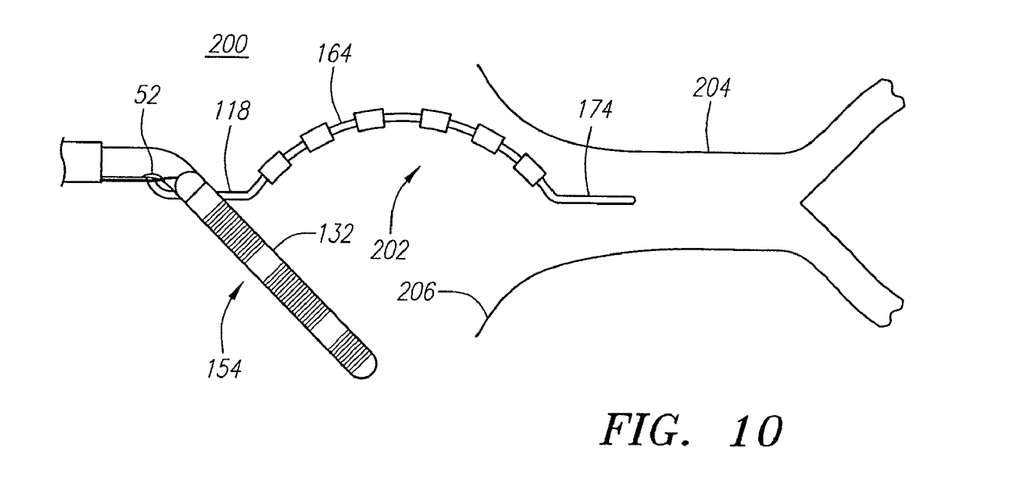

Having described the structure of the treatment system 110, its operation in creating a circumferential lesion around the ostium of a pulmonary vein, thereby electrically isolating it from the left atrium of the heart, will now be described with reference to FIGS. 9-11. Once the guide sheath 14 has been properly placed within the left atrium 202 of the heart 200, as described above with reference to FIG. 4, the ablation catheter 116 is introduced through the guide sheath 14 until the ablative structure 132 is deployed from the guide sheath 14, as illustrated in FIG. 9. The ablative structure 132 is placed into a loop-shaped by pulling the pull wire 134, and the mapping catheter 118 is then introduced into the entry port 50 on the handle assembly 31 (shown in FIG. 1), through the lumen of the ablation catheter 116 until the mapping structure 164 is deployed out from the exit port 52 through the interior space 154 formed by the ablative structure 132, as illustrated in FIG. 10. As previously mentioned, introduction of the mapping catheter 118 within the lumen of the ablation catheter 116 can either be accomplished prior to or subsequent to the introduction of the ablation catheter 116 within the left atrium 202 of the heart 200. Notably, the distal section 174 of the mapping catheter 118 is located within the ostium 206 of the pulmonary vein 204, so that it can be guided within the pulmonary vein 204 as the ablative structure 132 is advanced towards the ostium 206.

Figure 11:
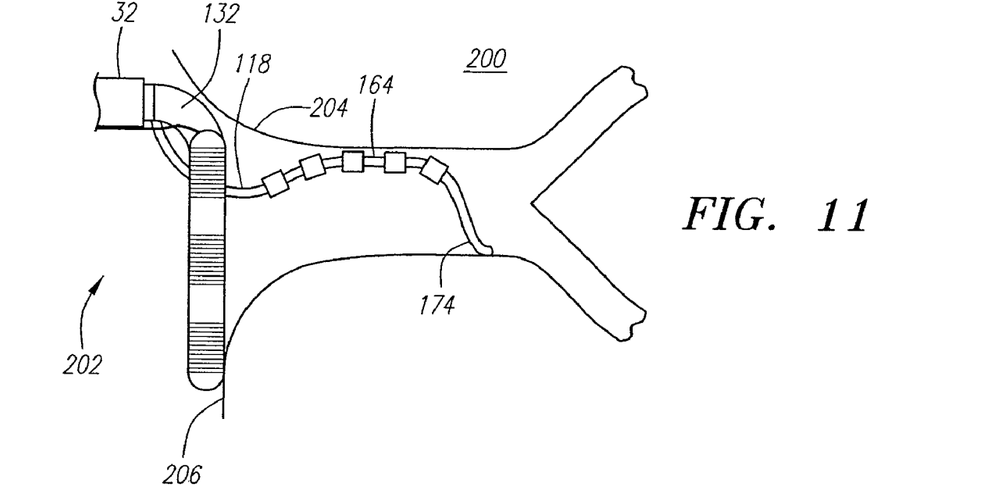

Once the distal section 174 of the mapping catheter 118 is definitively within the pulmonary vein 204, the ablative structure 132 is placed against the ostium 206 of the pulmonary vein 204, so that it circumscribes the ostium 206, as illustrated in FIG. 11. The resiliency of the ablative structure 132 places the ablation electrodes 34 in firm and stable contact with the ostium 206. The mapping structure 164 is placed firmly in contact with the tissue inside the pulmonary vein 204. Specifically, the mapping structure 164 is placed in contact along the wall of the pulmonary vein 204, and the distal straight section 174 is placed contralaterally in contact along the wall of the pulmonary vein 204.

In a similar manner previously described, the mapping processor 22 is operated to obtained pre- and post-ablation ECG signals, and the RF generator 20 is operated to create a circumferential lesion around the ostium 226 of the pulmonary vein 204.

Figure 12:
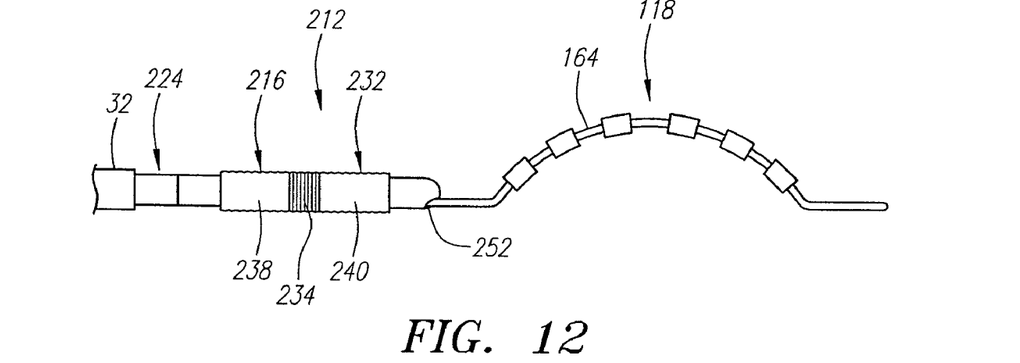
FIG. 12 is a plan view of still another ablation/mapping catheter assembly that can be used in the medical treatment system of FIG. 1, wherein a balloon electrode structure is particularly shown in a collapsed geometry.
Figure 13:
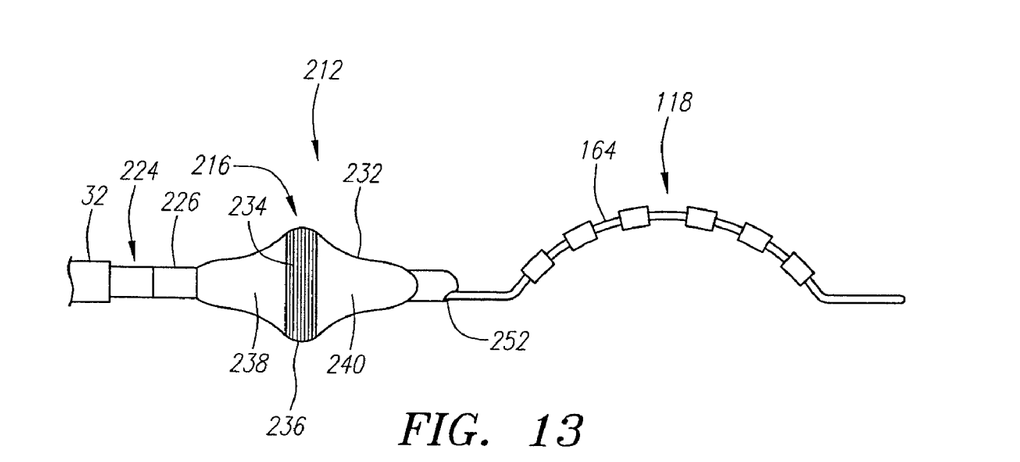
FIG. 13 is a plan view of the catheter assembly of FIG. 12, wherein the balloon electrode structure is particularly shown in an expanded geometry.

Referring now to FIGS. 12 and 13, another alternative embodiment of a catheter assembly 212 that can be used in the treatment system 10 of FIG. 1 is shown. The catheter assembly 212 is similar to the previously described catheter assembly 12, with the exception that an expandable-collapsible ablative structure, rather than a helically-shaped ablative structure, is formed at the distal end of the ablation catheter body.

Specifically, an ablation catheter 216 comprises a flexible elongate catheter body 224 having a distal member 226 on which there is mounted an expandable-collapsible ablative structure 232. The ablative structure 232 is formed by a "balloon-like" wall suitably bonded to and disposed about the distal member 226. The geometry of the ablative structure 232 can be altered between a collapsed, low profile geometry (FIG. 12), and an expanded, high profile geometry (FIG. 13). The ablation catheter body 224 comprises inflation and venting lumens (not shown) that extend from a handle assembly (not shown) to the interior region of the ablative structure 232. The catheter body 224 comprises a lumen (not shown) that terminates in an exit port 252 out which the previously described mapping structure 164 of the mapping catheter 118 extends. The exit port 252, in this case, is distal to the ablative structure 232.

In order to inflate the ablative structure 232, a liquid inflation medium, such as water, saline solution, or other biocompatible fluid, is conveyed under positive pressure through a port on the handle assembly, through the inflation lumen extending through the catheter body 224. The liquid medium fills the interior of the ablative structure 232 and exerts pressure on the inside of the ablative structure 232 to urge the ablative structure from its collapsed geometry (FIG. 12) to its expanded geometry (FIG. 13). Constant exertion of pressure through the inflation lumen maintains the ablative structure 232 in its expanded geometry. The venting lumen is used to vent any air or excess fluid from the ablative structure 232. Alternatively, the inflating fluid medium can comprise a gaseous medium, such as carbon dioxide.

Preferably, the ablative structure 232 is less than 8 French diameter when in a collapsed geometry for ease of manipulation through the vasculature, and about 2.0 cm in circumference around its largest portion when in its expanded geometry and located in a desired ablation region within the pulmonary vein. The ablative structure 232 is preferably made of a suitable biocompatible, thermoplastic or elastomeric material, and can be configured to have any one of many shapes in its expanded geometry, such as the shape shown in FIG. 13, depending on the desired resulting geometry.

Proximate the center of the ablative structure 232 is a pronounced circumferential region 236 having a larger circumference than that of the rest of the ablative structure 232. In this manner, expansion of the ablative structure 232 within the pulmonary vein provides a force that is concentrated between the enlarged circumferential region 236 and the interior surface of a pulmonary vein in which the ablative structure 232 is situated, thus enhancing the lesion creating characteristics of the ablative structure 232.

The ablation catheter 216 comprises an electrode that takes the form of a conductive shell 234 made of a material having a relatively high electrical and thermal conductivity that is suitably deposited on the outer surface of the ablative structure 232 over the enlarged circumferential region 236 using ion deposition or equivalent techniques. Materials possessing these characteristics include, among others, gold, platinum, platinum/iridium, conductive ink epoxy, or a combination thereof. In particular, noble metals are preferred.

The area of the ablative structure 232 located immediately proximal and distal to the enlarged circumferential region 236 is preferably masked prior to the deposition of the conductive material, so that resulting non-conductive regions 238 and 240 are formed on either side of the conductive shell 234. In particular, the masking of the regions on either side on the conductive region assures that the maximum current density will be distributed at the enlarged circumferential region 236 of the ablative structure 232, thereby allowing the ablative structure 232 to efficiently form annular lesions within the pulmonary vein. In order to deliver current, the conductive shell 234 is coupled to a plurality of insulated ablation wires (not shown), that are in turn coupled to the handle assembly (not shown).

There are many modifications that can be made to the ablative structure 232. For example, the conductive shell 234 may be segmented instead of continuous. The ablative structure 232 may be microporous, allowing ions to pass from an interior electrode, through the pores, into the tissue. The ablative structure 232 may have an interior support structure (such as resilient splines or mesh or a foam substance) arranged to apply an outward force against the electrode structure 232 to augment, or replace, the outward force caused by a pressurized liquid medium. The ablative structure 232 may comprise blood lumens for allowing the flow of blood through the ablative structure 232 when expanded within the pulmonary vein. The ablative structure 232 may be shaped, such that a portion of the conductive shell 234 engages the ostium of the pulmonary vein.

Other types of ablative structures, besides balloon-like ablative structures, can be envisioned. For example, a basket-type ablative structure having a plurality of resilient splines with ablation electrodes mounted thereon can be used to create a circumferential lesion within the pulmonary vein. Pre-shaped ablative loop structures that are either coplanar with, or orthogonal to, the longitudinal axis of the catheter body can also be used to create lesions within or around the pulmonary vein. The details regarding the ablative structure 232, as well as many other structures designed to create lesions in and around the pulmonary veins are disclosed in U.S. patent application Ser. No. 08/984,414, which is expressly incorporated herein by reference. In each case, a lumen for housing the mapping catheter 118, and an exit port out which the mapping electrode structure 164 extends, can be incorporated into the design.

Figure 14:
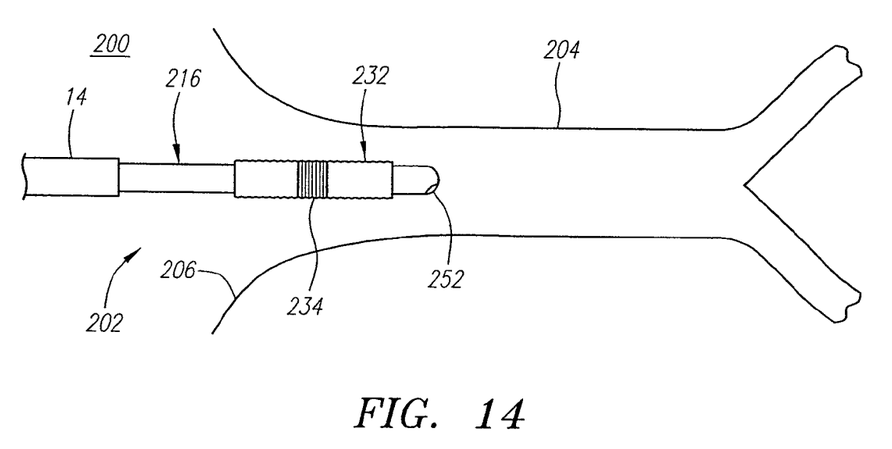
FIGS. 14-16 are plan views of a method of using the catheter assembly of FIG. 12 to create a circumferential lesion within the ostium of a pulmonary vein.
Figure 15:
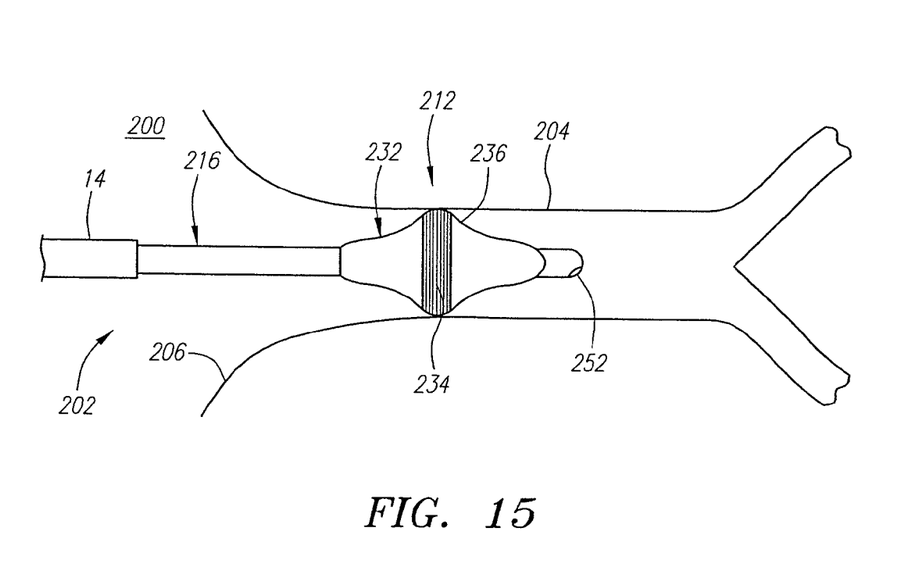

Having described the structure of the treatment system 210, its operation in creating a circumferential lesion around the ostium of a pulmonary vein, thereby electrically isolating it from the left atrium of the heart, will now be described with reference to FIGS. 14-16. Once the guide sheath 14 has been properly placed within the left atrium 202 of the heart 200 adjacent the ostium 206 of the selected pulmonary vein 204, as described above with reference to FIG. 4, the ablation catheter 216, while the ablative structure 232 is in its collapsed state, is introduced through the guide sheath 14 until the ablative structure 232 is deployed from the guide sheath 14 and into the ostium 206 of the pulmonary vein 204, as illustrated in FIG. 14. The ablative structure 232 is then is placed into its expanded geometry by conveying the inflation medium into the interior of the ablative structure 232, so that the enlarged circumferential region 236 is circumferentially placed firmly in contact with the inner wall of the pulmonary vein 204, as illustrated in FIG. 15. The mapping catheter 118 is then introduced through the lumen of the ablation catheter 216 until the mapping structure 164 is deployed out from the exit port 252. As previously mentioned, introduction of the mapping catheter 118 within the lumen of the ablation catheter 216 can either be accomplished prior to or subsequent to the introduction of the ablation catheter 216 within the left atrium 202 of the heart 200.

Figure 16:
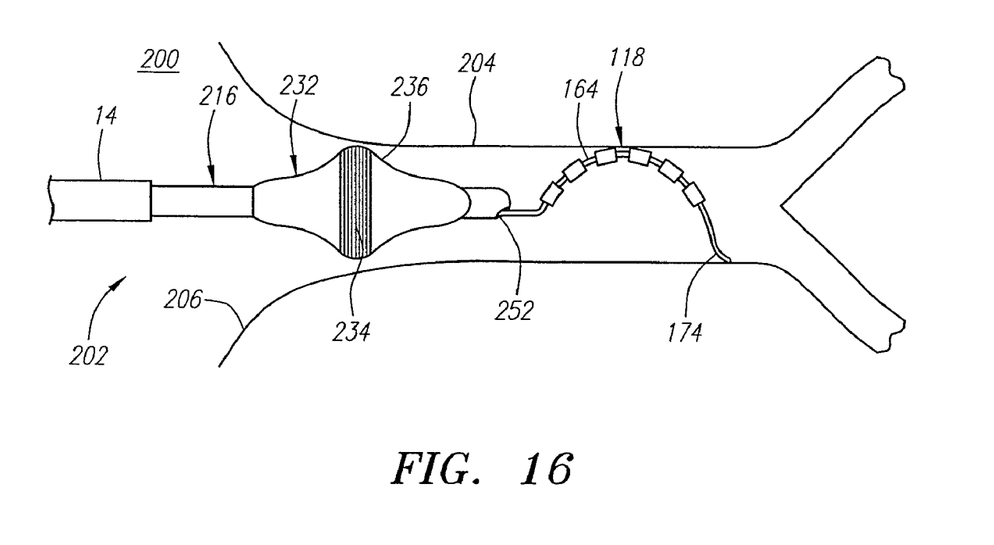

As illustrated in FIG. 16, the mapping structure 164 is placed firmly in contact with the tissue inside the pulmonary vein 204. Specifically, the mapping structure 164 is placed in contact along the wall of the pulmonary vein 204, and the distal straight section 174 is placed contralaterally in contact along the wall of the pulmonary vein 204. In a similar manner previously described, the mapping processor 22 is operated to obtain pre- and post-ablation ECG signals, and the RF generator 20 is operated to create a circumferential lesion within the pulmonary vein 204.

Figure 17:
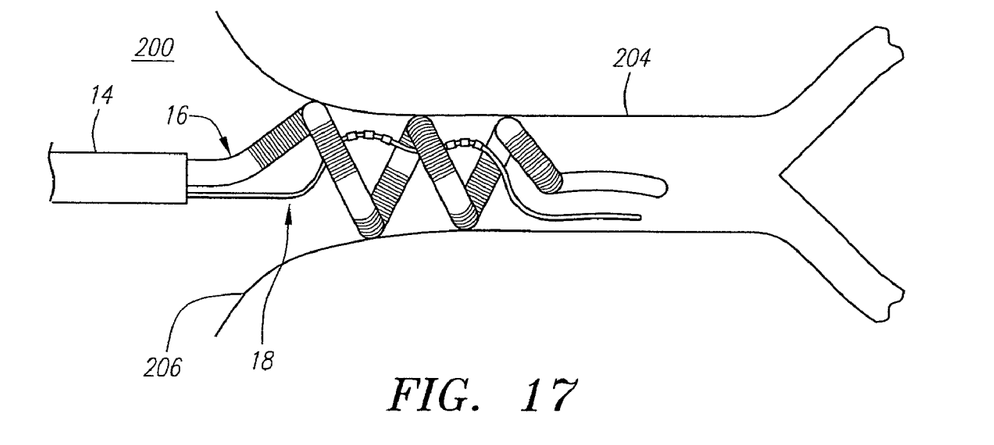
FIG. 17 is a plan view showing a method of using yet another ablation/mapping catheter assembly to create a circumferential lesion within the ostium of a pulmonary vein.

In all of the previously described embodiments, the mapping catheters have been introduced through lumens contained within the ablation catheters. Alternatively, as illustrated in FIG. 17, the ablation catheter 16 and mapping catheter 18 can be independently introduced through the lumen of the guide sheath 14. Thus, the steps used to create a circumferential lesion within the pulmonary vein 204 using this assembly will be the same as that described with respect to FIGS. 4-6, with the exception that the mapping catheter 18 will be introduced through the lumen of the guide sheath 14, rather than a lumen within the ablation catheter 16.

Although particular embodiments of the present invention have been shown and described, it will be understood that it is not intended to limit the present invention to the preferred embodiments, and it will be obvious to those skilled in the art that various changes and modifications may be made without departing from the spirit and scope of the present invention. Thus, the present inventions are intended to cover alternatives, modifications, and equivalents, which may be included within the spirit and scope of the present invention as defined by the claims.

What is claimed is:

1. A probe for ablating tissue, comprising:
   an elongate probe body having a main member disposed in a first plane, and a distal member configured for forming a loop-shaped structure, wherein the probe body is pre-shaped in a manner that disposes the loop-shaped structure in a second plane in the range of 30 to 60 degrees with the first plane; and
   one or more ablative elements mounted to the loop-shaped structure, wherein the one or more ablative elements are arranged to create a circumferential lesion.

2. The probe of claim 1, wherein the probe body is an intravascular catheter body.

3. The probe of claim 1, wherein the loop-shaped structure is configured to be disposed around the ostium of a pulmonary vein, and the one or more ablative elements are configured to circumferentially contact tissue around the ostium of the pulmonary vein.

4. The probe of claim 1, further comprising a lumen extending through the probe body, the lumen configured to slidably receive an inner elongate probe body, the lumen having an exit port out which the inner probe body can extend through the loop-shaped structure.

5. The probe of claim 4, wherein the exit port is proximal to the loop-shaped ablative structure.

6. The probe of claim 1, further comprising a pull-wire connected to the distal member, wherein the pull-wire is configured for being pulled to form the distal member into the loop-shaped ablative structure.

7. The probe of claim 1, wherein the second plane is out-of-plane with the first plane by 45 degrees.

8. The probe of claim 1, wherein the probe body further includes a resilient core wire that pre-shapes the probe body in a manner that disposes the loop-shaped structure in the second plane.

9. A probe assembly for ablating tissue, comprising:
   an outer probe including an elongate probe body having a main member disposed in a first plane, and a distal member configured for forming a loop-shaped ablative structure, wherein the probe body is pre-shaped in a manner that disposes the loop-shaped structure in a second plane in the range of 30 to 60 degrees with the first plane, the outer probe further including a lumen having an exit port, and one or more ablative elements mounted to the loop-shaped ablative structure; and
   an inner probe configured to be slidably disposed within the lumen of the outer probe, the inner probe including an elongate probe body having a distal diagnostic structure configured to extend out the exit port and through the loop-shaped structure, and one or more diagnostic elements mounted to the distal diagnostic structure.

10. The probe assembly of claim 9, wherein the outer probe body is an intravascular catheter body.

11. The probe assembly of claim 9, wherein the loop-shaped ablative structure is configured to be disposed around the ostium of a pulmonary vein, and the one or more ablative elements are configured to circumferentially contact tissue around the ostium of the pulmonary vein.

12. The probe assembly of claim 9, wherein the distal diagnostic structure comprises a single spline.

13. The probe assembly of claim 9, wherein the distal diagnostic structure is configured to assume a curvilinear shape.

14. The probe assembly of claim 9, wherein the one or more diagnostic elements comprises one or more electrophysiology mapping elements.

15. The probe assembly of claim 9, further comprising a guide sheath for housing the outer probe.

16. The probe assembly of claim 9, wherein the exit port is proximal to the loop-shaped ablative structure.

17. The probe assembly of claim 9, further comprising a pull-wire connected to the distal member, wherein the pull-wire is configured for being pulled to form the distal member into the loop-shaped ablative structure.

18. The probe assembly of claim 9, wherein the second plane is out-of-plane with the first plane by 45 degrees.

19. The probe assembly of claim 9, wherein the probe body further includes a resilient core wire that pre-shapes the probe body in a manner that disposes the loop-shaped structure in the second plane.

* * * * *